(12) United States Patent
Touchard et al.

(10) Patent No.: US 9,750,635 B2
(45) Date of Patent: *Sep. 5, 2017

(54) EYE INJECTION DEVICE

(71) Applicant: INSTITUT NATIONAL DE LA SANTE ET DE LA RECHERCHE MEDICALE, Paris (FR)

(72) Inventors: Elodie Touchard, Paris (FR); Laura Kowalczuk, Paris (FR); Francine Behar-Cohen, Paris (FR)

(73) Assignee: INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 106 days.

This patent is subject to a terminal disclaimer.

(21) Appl. No.: 14/698,281

(22) Filed: Apr. 28, 2015

(65) Prior Publication Data

US 2015/0238356 A1  Aug. 27, 2015

Related U.S. Application Data

(63) Continuation of application No. 12/921,979, filed as application No. PCT/FR2009/000260 on Mar. 12, 2009, now Pat. No. 9,180,044.

(30) Foreign Application Priority Data

Mar. 14, 2008  (FR) ..................... 08 01415

(51) Int. Cl.
*A61F 9/00* (2006.01)
*A61N 1/32* (2006.01)
*A61N 1/30* (2006.01)

(52) U.S. Cl.
CPC .......... *A61F 9/0008* (2013.01); *A61F 9/0017* (2013.01); *A61F 9/0026* (2013.01); *A61N 1/327* (2013.01); *A61N 1/306* (2013.01)

(58) Field of Classification Search
CPC .... A61F 9/0017; A61F 9/0026; A61F 9/0008; A61N 1/327; A61N 1/306
See application file for complete search history.

(56) References Cited

U.S. PATENT DOCUMENTS

| 4,990,150 A | 2/1991 | Tsubota et al. |
| 6,154,671 A | 11/2000 | Parel et al. |

(Continued)

FOREIGN PATENT DOCUMENTS

| CA | 2 325 428 A1 | 8/2001 |
| JP | H09-266954 A | 10/1997 |

(Continued)

OTHER PUBLICATIONS

Written Opinion of the International Searching Authority issued in corresponding International Application No. PCT/FR2009/000260 mailed Aug. 11, 2009.

(Continued)

*Primary Examiner* — Bradley Osinski
(74) *Attorney, Agent, or Firm* — Oliff PLC

(57) ABSTRACT

An injection device for injecting a product into an eye, said device comprising an injection needle and a support on which the injection needle is fixed, said device being characterized in that it comprises a locating mark disposed in such a way that the latter can be placed in contact with a defined bearing region of the surface of the eye, before any contact of the injection needle with said surface, and can then be kept in contact with said bearing region during a stage of penetration of said injection needle through said surface of the eye.

19 Claims, 5 Drawing Sheets

(56) References Cited

U.S. PATENT DOCUMENTS

| | | |
|---|---|---|
| 8,460,242 B2 | 6/2013 | Paques et al. |
| 9,180,044 B2 * | 11/2015 | Touchard .............. A61F 9/0017 |
| 2004/0167458 A1 | 8/2004 | Draghia-Akli et al. |
| 2006/0253124 A1 | 11/2006 | Greenberg et al. |
| 2007/0156082 A1 | 7/2007 | Scherman |

FOREIGN PATENT DOCUMENTS

| | | |
|---|---|---|
| JP | H11-244323 A | 9/1999 |
| JP | 2001-259046 A | 9/2001 |
| WO | 00/07530 A2 | 2/2000 |
| WO | 03/070297 A2 | 8/2003 |
| WO | 2006/052557 A2 | 5/2006 |
| WO | 2006/123248 A2 | 11/2006 |
| WO | 2007/052730 A1 | 5/2007 |

OTHER PUBLICATIONS

May 21, 2013 Notice of Reasons for Rejection issued in Japanese Patent Application No. 2010-550233.
International Search Report issued in corresponding International Application No. PCT/FR2009/000260 mailed Aug. 31, 2009.

\* cited by examiner

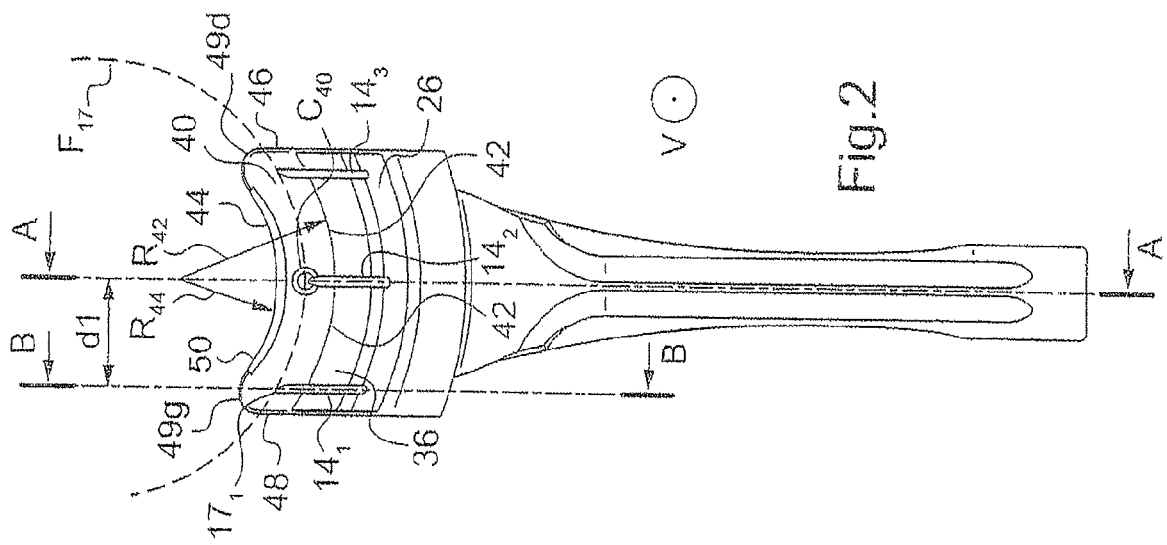
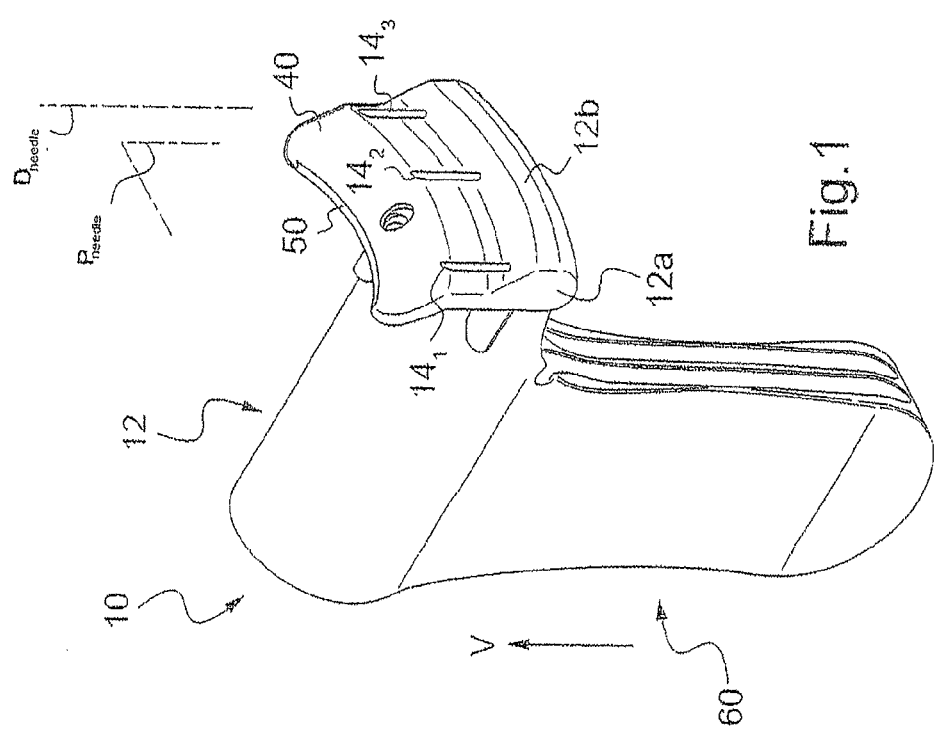

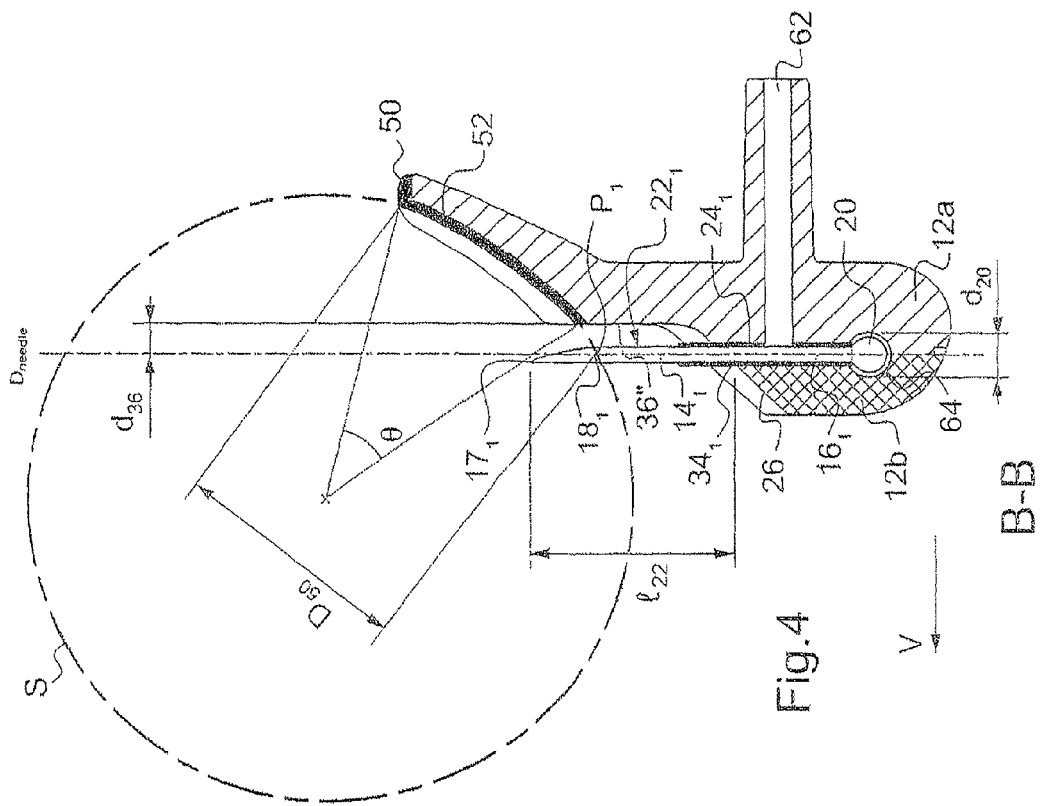
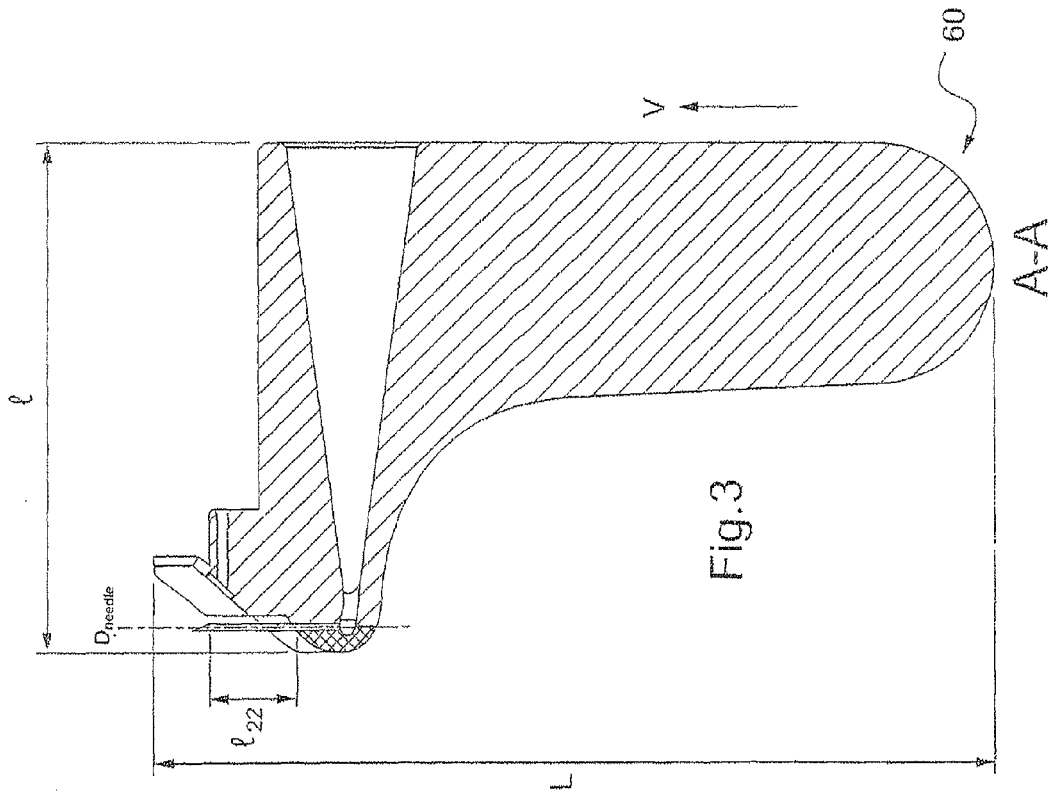

B-B

EYE INJECTION DEVICE

This is a continuation application of application Ser. No. 12/921,979 filed Jan. 24, 2011 which is a national stage application of International Application No. PCT/FR2009/000260 filed Mar. 12, 2009, and claims the benefit of priority from French Patent Application No. FR 08 01415, filed Mar. 14, 2008. The disclosures of the prior applications are hereby incorporated by reference herein in their entirety.

TECHNICAL FIELD

The present invention relates to a device for injecting a product into an eye and/or for electroporation.

PRIOR ART

WO 2006/123248 describes a device for administering a product by electroporation. In the embodiment shown in FIG. 16, the device is designed such that it can be applied to the surface of the eye and it has a needle permitting an injection of product. The placement of this device on the surface of the eye is awkward. In addition, the positioning is relatively imprecise. Finally, an error in positioning requires multiplying the punctures in the eye in order to reposition the device.

WO 00/07530, WO 2007/052730 and WO 2006/052557 describe injection devices. These devices do not comprise an injection needle fixed on a support designed to bear on the surface of the eye, nor do they have a locating mark designed to bear on the edge of the cornea of an eye before any contact of the injection needle with the eye, and then to be kept in this bearing position during the stage of penetration of said injection needle into the eye.

SUMMARY OF THE INVENTION

It is an object of the invention to make available an injection device with which one or more of the abovementioned problems can be solved at least in part.

To this end, the invention proposes, in a first main embodiment, an injection device for injecting a product into an eye (that is to say into the ocular media or into a tissue of the eye), said device comprising:
  an injection needle,
  a support on which the injection needle is fixed or which is able to guide a sliding movement of the injection needle,
said device comprising a locating mark disposed in such a way that said locating mark can be placed in contact with a defined bearing region of the surface of the eye before any contact of the injection needle with said surface, and can then be kept in contact with said bearing region during a stage of penetration of said injection needle through said surface of the eye.

As will be set out in more detail later in the description, the locating mark allows the user to position the injection device, with remarkable precision, on the surface of the eye before any penetration of the injection needle through the surface thereof. The risk of error is therefore reduced or substantially eliminated.

In one embodiment, particularly intended for an injection into a vitreous cavity, the locating mark is disposed in such a way that, during said stage of penetration of the injection needle through the surface of the eye, the distance between the bearing region of the locating mark on the eye and the point of penetration of the needle into the eye (corresponding to the distance $D_{50}$ in FIG. 4 and to the distance $D_{50}"$ in FIG. 8) is greater than 2 mm, greater than 3 mm, or greater than 3.5 mm and/or less than 6 mm, less than 5 mm, or less than 4.5 mm. A distance of 4 mm is ideal.

Particularly when the device is designed for an injection into a ciliary muscle, this distance can be greater than 1 mm, greater than 1.5 mm and/or less than 4 mm, less then 3 mm, or less than 2.5 mm. A distance of 2 mm is ideal.

In addition, the locating mark is disposed in such a way that it can be kept in contact with the bearing region during at least part, preferably during the entirety, of the penetration of the injection needle through the surface of the eye. The user is thus provided with a useful aid for controlling and suppressing any inopportune movement of the support during the stage of penetration of the injection needle into the eye. In particular, in one embodiment, the locating mark is designed to cooperate with the bearing region in such a way as to limit or even eliminate the possibility of a movement of the locating mark relative to the bearing region during the stage of penetration of the injection needle.

Said bearing region can in particular comprise a part of the edge of the cornea, that is to say of the transition shoulder between the cornea and the sclera, called the "limbus".

A locating mark ensuring a bearing area of greater than 5 mm, greater than 7 mm, or greater than 9 mm on this edge advantageously permits good stabilization of the device during the stage of penetration.

Said injection needle can be designed in such a way that its distal end reaches the ciliary muscle or the vitreous cavity, or the subretinal space, or the retina, or the pigment epithelium of the retina, or the corneal epithelium or stroma or endothelium or transcornea, or else the peri-ocular muscles. Means are preferably provided to ensure that this distal end cannot be engaged beyond these elements during the stage of penetration, the bearing region being at least a part of the edge of the cornea of the eye.

The locating mark and the injection needle can be configured in such a way that the angle between the direction of penetration and the direction perpendicular to the surface of the eye at the point of penetration is less than 20°, or 15°, 10°, or 5° throughout the stage of penetration. The length of the injection needle introduced into the eye is then advantageously reduced.

Needle

The external diameter of the injection needle can be between 0.2 and 0.4 mm.

The protruding part of the injection needle, that is to say the part protruding from the support, can be greater than 2 mm, or greater than 3 mm, or greater than 3.3 mm and/or less than 5 mm, or less than 4 mm, or less than 3.7 mm.

The tip, or "distal end", of the injection needle can be beveled in order to facilitate its insertion into the eye. The injection needle can open out axially and/or radially at its distal end. Preferably, the injection needle opens out axially. Still more preferably, it is tapered, that is to say conical along the axis of the needle, and opens out axially.

The shape of the injection needle is not limiting.

The injection needle can be substantially rectilinear. It can also extend along an arc of a circle centered on a point of the locating mark, in particular in order to facilitate its insertion by rotation of the support about the bearing region.

In order to effectively fix the injection needle, the base of the latter can be sandwiched between a main part of the support and a blocking piece fixed to said main part of the support.

The device can comprise several injection needles and in particular can comprise three, or more than three, injection needles, these being identical or different.

The injection needles can have an identical total length, whichever injection needle is considered.

The protruding parts of the injection needles can be identical or different. They can in particular be of the same length.

The injection needles can all be fixed in the same way on the support.

In one variant of the invention, one or more of the injection needles are not fixed on the support but instead can slide on the latter during the stage of penetration. These needles can be removable or can be mounted integrally on the support, that is to say in such a way as to remain joined to the support.

In the latter case, they can advantageously be retractable into said support.

In one embodiment, the injection needles are spaced apart from one another, pair by pair, by a distance of greater than 3 mm, or greater than 3.5 mm, or greater than 4 mm and/or less than 6 mm, or less than 5.5 mm, or less than 5 mm.

The injection needles can be substantially parallel and/or coplanar.

The distal ends of the injection needles can extend along a line, for example presenting a plane of symmetry. This line can be rectilinear, for example. It can also be curved, for example following an arc of a circle. In particular, when the support comprises a spherical abutment face, as is described later, this line can have the same radius of curvature as this abutment face or can be concentric to the latter.

The distal ends of the injection needles may not belong to one and the same plane perpendicular to the local direction of said injection needles in the area of their distal ends.

In one embodiment, the proximal ends of the injection needles, that is to say the ends remote from the distal ends, open into a distribution channel common to all the injection needles, the distribution channel being formed, for example, in the support. The support can then have connection means for establishing a fluid communication between the distribution channel and a source of the product that is to be injected.

In one embodiment, the device also has means for selectively or simultaneously plugging one or more, preferably all, of the lumens of the injection needle or needles, for example in the area of the proximal ends or of the distribution channel.

These means can in particular comprise one or more stoppers, each designed to plug one or more injection needles.

In one embodiment, each injection needle can be supplied independently of the others. For example, each needle can be connected to an individual tube. It is thus advantageously possible to inject different active principles through the different injection needles of the device.

In this embodiment, it is possible to cut the supply to the associated injection needle by clamping or pinching a tube.

All the tubes can also be connected to a main tube which, when clamped or pinched, causes the supply to all the tubes to be cut simultaneously.

Support

The support can be used for manipulation of the device. The support can in particular comprise a handle allowing the injection device to be gripped, for example, between a thumb and an index finger of one hand. Manipulation of the device is made easier in this way. This handle can in particular extend substantially along a general plane parallel to the injection needle or needles.

The length of the support can be greater than 10 mm or 30 mm and/or less than 100 mm, 50 mm or 40 mm. Its transverse width can be greater than 10 mm or 15 mm and/or less than 30 mm, or less than 25 mm.

The support can be made of a transparent material in order to allow the user to more easily observe the point of penetration of the needle.

In one embodiment, the support is designed to be able to keep the eyelids open during the stage of penetration of the injection needle. For this purpose, it can in particular comprise lateral edges, for example with a height of greater than 0.5 mm, 1 mm, 2 mm or 3 mm. To improve the hold of an eyelid on an edge, the support can also comprise a protuberance designed to take up a position between the surface of the eye and the eyelid when said eyelid bears on the edge.

The support thus advantageously serves as a means of spacing the eyelids, which ensures optimal safety and avoids any risk of sudden closure of the eyelids during the injection.

Abutment Means

The device can comprise abutment means that are designed to prevent penetration of the injection needle or needles into the eye beyond a defined position, called the "position of use".

The abutment means can comprise "abutment means of the support", which are designed to limit the movement of the support during the stage of penetration. In particular, when the support is set in motion during the stage of penetration, these abutment means of the support make it possible to prevent the continuation of this movement beyond a defined position, for example beyond a position where an abutment face of the support fits the surface of the eye. The abutment means of the support are thus designed to permit a positioning of the support on the eye in a defined position or "abutment position of the support". An abutment position of the support can in particular be obtained when the locating mark bears on the limbus of the eye and an abutment face of the support fits the sclera of the eye. When the injection needle or needles are fixed on the support, the position of use corresponds to the abutment position of the support.

In the embodiment in which an injection needle is mounted slidably on the support, the abutment means can also comprise "needle" abutment means designed to limit the length of said needle able to project from the support at the distal end of the needle, that is to say the length of the protruding part of the needle. The injection needle can, for example, have an area of excess thickness that can abut against the support. The expression "needle abutment position" designates the position of the needle corresponding to a maximum length of the protruding part of the needle, that is to say the position in which the needle abutment means are active. In this embodiment, the position of use preferably corresponds to a configuration in which the support is in an abutment position of the support and the injection needle is in a needle abutment position.

The abutment means are preferably designed in such a way as to limit to less than 20 mm, especially for an injection into the retina, less than 7 mm, or to less than 3 mm, especially for an injection into the ciliary muscle, or to less than 1 mm, or to less than 0.7 mm, the length by which the injection needle or needles can be inserted into the eye during a stage of penetration of the injection needle, or the "maximum length of insertion". The maximum length of insertion is preferably greater than 0.5 mm and less than 14 mm.

The abutment means of the support preferably comprise an abutment face which is designed to come into contact with the surface of the eye and preferably has a shape matching this surface, in particular matching the sclera of the eye, in such a way that, in the abutment position of the support, it can fit the shape of said eye and thereby ensure a reliable positioning.

The abutment face can comprise non-slip means designed to limit the sliding movement of the device in the abutment position of the support.

In one embodiment, the abutment face has a surface area of greater than 4 mm$^2$ and/or less than 21 mm$^2$. The abutment face can be solid or can be locally interrupted by holes.

The abutment face can have a spherical shape, the radius of curvature R being in particular greater than 9 mm, 10 mm or 11 mm and/or less than 14 mm, less than 13 mm, or less than 12 mm. A radius of curvature of 11.75 mm is ideal.

The abutment face preferably extends laterally, that is to say in its greatest dimension as seen from the front, over an angle sector α of greater than 45°, preferably greater than 60°, or 70°, 75°, or even 80° and/or less than 135°, preferably less than 120°, or 100°, 95°, or even 90°.

The abutment face preferably extends in height, that is to say in its smallest dimension as seen from the front, over an angle sector θ of greater than 15°, or greater than 25°, or even 30° and/or less than 55°, or less than 45°, or even 40°.

Preferably, the abutment face does not extend over more than one quadrant of a hemisphere.

Seen from the front, the abutment face can have a substantially parallelepipedal contour, for example a rectangular contour.

The abutment face can have two large sides and two small sides. The large sides can in particular form rounded corners with the small sides.

The length of the small sides can be greater than or equal to 2 mm and/or less than 3 mm. The length of the large sides can be greater than 2 mm and/or less than 7 mm.

The abutment face is preferably designed to come into contact with the surface of the eye only at the end of the stage of penetration of the injection needle.

It is also preferable, in the abutment position of the support, that the support bears on the surface of the eye only by way of the abutment face.

In the case where the injection needles are coplanar, the plane of the needles can be substantially parallel to the large sides.

The main axis of the abutment face designed to come into contact with the eye can be inclined with respect to the direction of one or more of the needles or, if these needles are coplanar, with respect to the plane in which they extend, by an angle δ of greater than 20° and/or less than 85°.

Particularly in the case where the injection device is designed for an injection into a ciliary muscle, the angle δ can be greater than 30°, 40°, 50° and/or less than 80°, 70°, 60°. An angle of about 55° is ideal.

In one embodiment, particularly in the case where the injection device is designed for an injection within the vitreous cavity, the angle δ can be determined in such a way that the injection needle or needles extend substantially in a direction passing through the center C of a spherical envelope S along which the abutment face extends. It can then be advantageous that, in the abutment position of the support, at least one of the injection needles passes through the center of the eye.

Particularly when the device is designed for an injection into the vitreous cavity, the angle δ can be greater than 20°, greater than 30° and/or less than 45°, or less than 40°, with an angle of about 35° being ideal.

In one embodiment, the device comprises an abutment face extending substantially along a spherical envelope, and the locating mark extends along a locating line in the shape of an arc of a circle whose axis passes through the center of said spherical envelope.

The spherical envelope and the arc of a circle can in particular be determined in such a way that, in the position of use, the abutment face bears completely on the sclera of the eye, and the locating mark bears completely on the edge of the cornea.

In one embodiment, the device comprises an abutment face extending substantially along a spherical envelope, the locating mark extends along a locating line in the shape of an arc of a circle, at least one needle penetrates into the spherical envelope via a point of penetration and, in a plane passing through the center of said spherical envelope, via said point of penetration, and perpendicularly intersecting said arc of a circle, the distance between said point of penetration and the point of said arc of a circle through which said plane intersects said arc of a circle is (1) greater than 1 mm, preferably greater than 1.5 mm, more preferably greater than 1.8 mm and less than 3 mm, preferably less than 1.5 mm, more preferably less than 1.2 mm, said needle extending inside said spherical envelope to a depth of greater than 0.5 mm, preferably greater than 0.6 mm, more preferably greater than 0.8 mm, and less than 1.5 mm, preferably less than 1.3 mm, more preferably less than 1.2 mm; or (2) greater than 2 mm, preferably greater than 3 mm and less than 4.5 mm, preferably less than 4 mm, or less than 3.5 mm, said needle extending inside said spherical envelope to a depth of greater than 6 mm, preferably greater than 8 mm, and less than 15 mm, preferably less than 13 mm.

Preferably, all the needles simultaneously meet condition (1), this embodiment being particularly ideal for an injection into the ciliary muscle of the eye, or condition (2), this embodiment being particularly ideal for an injection into the vitreous body.

The depth is the minimum distance between the surface of the spherical envelope and the distal end of the needle in question, that is to say usually the distance between this surface and this distal end as measured on a radius of the spherical envelope S.

Preferably, all the needles extend inside the spherical envelope to an identical depth.

Preferably, the injection needle or needles are engaged on the support on the same side as the abutment means, with respect to the locating mark.

In one embodiment, the injection needle or needles do not pass through the abutment face. They can in particular emerge from an "insertion face" which, in the abutment position of the support, is not in contact with the eye. The spacing between the eye and the insertion face advantageously allows the user to observe the surface of the eye near the point of penetration of the needle. It also facilitates the positioning of the support.

The insertion face can be set back relative to the abutment face and can, for example, be designed in such a way that, in the abutment position of the support, it is spaced apart from the surface of the eye by a distance greater than 1 mm and/or less than 1 cm.

The abutment means of the support can be fixed on the support or can be formed integrally therewith.

The abutment means of the support are preferably defined in such a way that, in the abutment position of the support, the needle or needles are inclined in a predefined direction and are preferably immobilized with respect to the surface of the eye.

When the support comprises means for guiding an injection needle, in order to guide a sliding movement thereof, needle abutment means can advantageously be provided in order to limit the length of the injection needle protruding in the deployed position of this injection needle.

Of course, a device according to the invention can comprise one or more injection needles fixed on the support and one or more injection needles able to slide on said support.

Locating Mark

The locating mark can vary considerably in shape. In particular, the locating mark can be formed by a point, at least 2 points, at least 3 points, or by all or part of a line, called "locating line", or by a surface.

In one embodiment, the device comprises a locating line able to match the surface of the eye, for example the edge of the cornea. It can follow an arc of a circle with a radius of greater than 5 mm or 6 mm and/or less than 8 mm or 7 mm, a radius of 6.58 mm being ideal.

Preferably, the locating line is at least partly, preferably entirely, convex toward the point of insertion of the needle in the support. In the case where the locating line follows an arc of a circle, said point of insertion is preferably outside the virtual spherical surface of which a great circle includes the locating line.

Preferably, when the abutment means comprise a substantially spherical abutment face, the point of insertion of the needle in the support and, preferably, all the points of insertion of all the needles is/are outside the virtual spherical surface on which the abutment face extends.

The length of the locating line that is in contact with the surface of the eye can depend on the degree of penetration of the injection needle or needles. For example, at the start of the stage of penetration, the locating line can be in contact via one or more points, or one or more fractions of this line, with the surface of the eye, then, during the penetration, the nature of this contact can change.

Preferably, the length of the locating mark is sufficiently short to ensure that, given the flexibility of the eye, the locating mark can remain along its entire length in contact with the edge of the cornea of the eye, throughout the stage of penetration. To make it easier to keep the locating mark in contact with the edge of the cornea throughout the stage of penetration of the injection needle, the locating mark is preferably designed to bear only along a length of less than 20 mm, less than 17 mm, or less than 15 mm of this edge.

The locating mark can be fixed on the support, on the abutment means or on any other element rigidly joined to the support. However, it must be immovable with respect to the support, at least during the stage of penetration, preferably permanently.

The locating mark can be carried, for example, by one or more injection needles or, if appropriate, one or more invasive or non-invasive electrodes.

In one embodiment, the locating mark is carried by abutment means, for example by a large side of an abutment face, and in particular, in the case of an abutment face of substantially rectangular shape as seen from the front, by the large side farthest from the injection needles.

The locating mark can be carried by, or indeed formed by, an edge of a non-invasive electrode.

Since the locating mark is designed to be placed in contact with the surface of an eye, it preferably has a smooth surface and, more preferably, a surface without any roughness, especially in the form of sharp tips or edges that could damage the surface of the eye during the stage of penetration. It can be made of a flexible material, that is to say a material that is not aggressive with respect to the surface of the eye, for example polymers of silicone, of conductive sponge, in particular synthetic sponge, of polyester, of polyorthoester, of polymethyl methacrylate or of any other flexible medical-grade polymers and, preferably, it can be translucent.

The locating mark can in particular be formed by a band of flexible material with a width of greater than 1.5 mm and/or less than 5 mm extending, for example, along an edge, for example along the entire length, of abutment means or of a non-invasive electrode.

The locating mark can in particular be formed by a bead of silicone or of foam. Advantageously, the risk of injury to the limbus (edge of the cornea) is thereby reduced.

The abutment face and/or the locating mark can also comprise suction means for fixing on the surface of the eye in the abutment position of the support. These means can be passive (foam exposing a multiplicity of open cells, suction cups), that is to say able to fix themselves to the surface of the eye by simple pressing against this surface. They can also be active, that is to say require aspiration.

Advantageously, these suction means contribute to stabilizing the support in the abutment position of the support.

The locating mark and/or the abutment means of the support can be formed by or at least partially covered by a non-slip material that is able to limit the sliding movement on the surface of the eye.

As has been explained above, the locating mark is disposed in such a way that it can remain in contact with the surface of the eye during the penetration of the injection needle or needles through this surface.

In one embodiment, the locating mark is designed in such a way as to guide the penetration of the injection needle or needles into the eye while remaining in contact with the surface of the eye. In particular, the locating mark can serve as a point of rotation for the injection needle or needles during said penetration. An increase, during said penetration, of the surface of the locating mark in contact with the surface of the eye can also improve the precision of this penetration.

Guide Means

An injection needle can be fixed on the support, that is to say can be permanently immobilized on the support, or, as an alternative, can be mounted movably on the support, either releasably or non-releasably.

For this purpose, the support can have guide means, for example in the form of a slide rail that permits a guided sliding movement of the injection needle on the support.

The slide rail can in particular be a through-orifice with a cross section matching that of the injection needle it is intended to receive. The guide means can guide the injection needle in movements along the curve of the needle. In the case of a rectilinear needle, the injection needle is guided along its axis. A rotation about its axis remains possible.

Alternatively, the guide rail can also prevent such a rotation.

The span of the guide rail, that is to say the distance between the two farthest points of the guide rail, can be greater than 2 mm, greater than 3 mm, greater than 4 mm, or greater than 5 mm. A large span advantageously permits efficient guiding.

The injection needle can be releasable, that is to say can optionally be disconnected completely from the support.

The invention thus also relates to a device according to the invention that does not necessarily comprise an injection needle. In particular, the invention proposes a support comprising a locating mark disposed such that it can be placed in contact, along a contact line having a length of at least 2 mm, or at least 3 mm, 5 mm, 7 mm, 9 mm, or 11 mm, with the limbus of an eye, and can then be kept in a position bearing on the limbus while an injection needle and/or an invasive electrode moves, guided by the support.

The support can have one or more of the optional or necessary features of the supports of the devices according to the invention. In particular, it can comprise an abutment face having a shape matching the surface of the eye.

In one embodiment, the support is designed in such a way that the locating mark can be placed in contact, along said contact line, with the limbus of the eye, and the abutment face can be placed bearing on the surface of the eye, without an injection needle or an invasive electrode having had to come into contact with the eye.

Electrodes

In one embodiment, the device comprises at least one invasive or non-invasive electrode. Preferably, the device comprises an assembly of electrodes composed of first and second sets of electrodes designed to be connected electrically to first and second terminals, respectively, of an electrical generator.

The assembly of electrodes can in particular comprise electrodes disposed in such a way as to ensure electroporation, facilitating the transfer of the product emerging from the injection needle or needles.

In a particular embodiment, at least one ejection orifice of an injection needle of the device opens out between an electrode of the first set of electrodes and an electrode of the second set of electrodes in such a way that product can emerge from the injection needle in a zone that can be covered by an electrical field generated by said electrodes.

In one embodiment, one or more of the invasive electrodes, or all of the invasive electrodes, are electrically insulated over at least part of their length, for example by means of an insulating cover. In particular, the electrically insulated part of the protruding part can extend from the support by a length of between 0.5 mm and 3 mm, for example by about 1 mm, particularly when the invasive electrode is designed to be inserted in a ciliary muscle, or by between 10 mm and 14 mm or between 11 mm and 13 mm, for example by about 12 mm, particularly when the invasive electrode is designed to be inserted in a vitreous cavity, or more generally by a length of between 0.5 mm, or 1 mm, and 30 mm. The whole of the protruding part can be electrically insulated.

The part of an invasive electrode in contact with the support, called the "inserted part", can have a length of between 10 and 20 mm, for example about 15 mm. Preferably, the inserted part is electrically insulated from the support.

An injection needle can be made at least in part, or entirely, of an electrically conductive material so as to constitute an invasive electrode. When the device comprises several injection needles, one or more of these injection needles, or all of these injection needles, can constitute invasive electrodes. The first and second sets of electrodes can, for example, be formed by injection needles.

One or more of the optional features described above for the injection needle or needles of the device can be applied to one or more invasive electrodes of the device, whether or not these are injection needles.

In one embodiment, the device comprises three injection needles in fluid communication and belonging to one and the same set of electrodes.

The other set of electrodes can be formed, for example, by one or more non-invasive electrodes, which may or may not belong to the device.

Preferably, the device comprises one or more non-invasive electrodes. A non-invasive electrode can be flexible or rigid.

In one embodiment, the device comprises a rigid non-invasive electrode with an electrically conductive element designed to come into contact with the surface of the eye and preferably configured so as to match the shape of the latter.

Preferably, the conductive element comprises, or is formed by, a cover made of an electrically conductive material, covering at least part of, preferably almost all of, an abutment face as described above.

The conductive cover can, for example, extend across the whole abutment face except for an edge that is designed to serve as a locating mark and is preferably formed by a flexible material, as defined above. The conductive element can also comprise, or be formed by, a plurality of pins connected electrically to one another and disposed, preferably regularly, on the contact surface of an abutment face. The abutment face carrying the conductive element can have one or more of the optional features of the abutment face of the abutment means described above.

In one embodiment, the support has a concave, substantially spherical surface which, seen from the front, has a substantially rectangular shape, said surface being designed to serve as abutment means and being covered, at least in part, or almost entirely, by an electrically conductive cover that can serve as an electrode.

The device can further comprise electrical connection means, in particular electrical connection terminals, making it possible to electrically connect said electrode or electrodes to the terminals of an electrical generator.

The device can comprise a reservoir of product that is to be injected, in particular a reservoir integral with the support, and means, for transferring product from this reservoir to the injection needle or needles.

In a second main embodiment, the invention relates to an injection device for injecting a product into an eye, said device comprising a support and an injection needle, the injection needle being fixed on said support or the support being able to guide a sliding movement of said needle, said support having a concave contact surface designed to extend over not more than one quadrant of a hemisphere and adapted to match the shape of the surface of the eye, in particular the substantially spherical surface of the sclera. This contact surface can serve as an abutment face and/or a substrate for one or more electrodes, in particular non-invasive electrodes, and/or a substrate for a locating mark.

The other features, possibly optional, of the device of the first main embodiment described above, and in particular the features relating to the number of injection needles and electrodes, to their shape and arrangement, to the shape of the abutment face, or of the locating mark, can be applied optionally to the device of the second main embodiment.

In a third main embodiment, the invention relates to an injection device comprising:

an injection needle oriented in an injection needle direction, a support on which said injection needle is fixed or which can guide a sliding movement of the injection needle, abutment means that are able to limit the penetration of the injection needle in said injection needle direction, said abutment means having an abutment face, preferably of substantially spherical shape, said device being distinguished by the fact that the injection needle and the main axis of the abutment face extend in parallel planes, and that, in a projection in one of these planes, the direction of the injection needle forms an angle δ of greater than 20° and/or less than 85° with the main axis of the abutment face.

The other features, possibly optional, of the devices of the first and second embodiments described above can be applied optionally to the device according to the third main embodiment.

In a fourth main embodiment, the invention relates to an electroporation device for introducing a product into an eye, said device comprising:
an invasive electrode,
a support on which the invasive electrode is fixed or which can guide a sliding movement of said invasive electrode,
said device having a locating mark disposed in such a way that said locating mark can be placed in contact with a defined bearing region of the surface of the eye, before any contact of the invasive electrode with said surface, and can then be kept in contact with said bearing region during a normal penetration of said invasive electrode through said surface of the eye.

The invasive electrode can in particular be an injection needle.

In a fifth main embodiment, the invention relates to an electroporation device for introducing a product into an eye, said device comprising a support and an invasive electrode, the invasive electrode being fixed on said support or the support being able to guide a sliding movement of said needle, said support having a concave contact surface designed to extend over not more than one quadrant of a hemisphere and adapted to match the shape of the surface of the eye, in particular the substantially spherical surface of the sclera. This contact surface can serve as an abutment face and/or a substrate for one or more electrodes, in particular non-invasive electrodes, and/or a substrate for a locating mark.

In a sixth main embodiment, the invention relates to an electroporation device comprising:
an invasive electrode oriented in an invasive electrode direction,
a support on which said invasive electrode is fixed or which can guide a sliding movement of the invasive electrode,
abutment means, preferably integral with the support, that are able to limit the penetration of the invasive electrode in said invasive electrode direction, said abutment means having an abutment face, preferably of substantially spherical shape,
said device being distinguished by the fact that the invasive electrode and the main axis of the abutment face extend in parallel planes, or in one and the same plane, and that, in a projection in one of these planes, the invasive electrode direction forms an angle of greater than 20° and/or less than 85° with the main axis of the abutment face.

The features, possibly optional, of the devices of the three first main embodiments described above can be applied optionally to the devices of the fourth, fifth and sixth main embodiments.

In particular, the invasive electrode can have one or more of the features of the injection needle of the devices according to the three first main embodiments of the invention.

The device can in particular comprise three invasive electrodes that can be electrically connected to one and the same terminal of an electrical generator, it being possible for these three invasive electrodes to be designed and arranged like the injection needles of the three first main embodiments of the invention.

The invention also relates to an electroporation device comprising an injection device according to the invention with at least two electrodes and an electrical generator electrically connected to said electrodes so as to be able to generate an electrical field between said electrodes.

Preferably, the electrical generator is designed to promote the electroporation of a product injected into an eye by means of said injection device. Preferably, the injection device then comprises at least one invasive electrode and one non-invasive electrode.

The invention also relates to a method for injecting a product into an eye by means of a device according to the first main embodiment of the invention, said method comprising the following successive steps:
a) placing the locating mark in contact with a bearing region of the surface of the eye,
b) causing the injection needle or needles to penetrate into the eye while keeping said locating mark in contact with said bearing region.

The bearing region can in particular be an edge of the cornea at the interface between the cornea and the sclera.

In one embodiment, at step b), the injection needle or needles are rotated about the bearing region.

In one embodiment, in which the injection needle or needles slide relative to the support, step b) can result from a sliding movement of these injection needles relative to the support, the support having been immobilized by being pressed on the surface of the eye. In particular, this immobilization can result from the complementary shapes of the locating mark and the limbus of the eye.

The invention also relates to an electroporation method for introducing a product into an eye by means of a device according to the fourth main embodiment described above, said method comprising the following successive steps:
a) placing the locating mark in contact with a bearing region of the surface of the eye,
b) causing the invasive electrode or electrodes to penetrate into the eye while keeping said locating mark in contact with said bearing region,
c) generating an electrical field between said invasive electrode and another electrode, for example a non-invasive electrode also fixed on the electroporation device, the electrical field being adapted to promote said electroporation.

The bearing region can in particular be an edge of the cornea.

In one embodiment, at step b), the invasive electrode or electrodes are rotated about the bearing region.

In one embodiment, in which the invasive electrode or electrodes slide relative to the support, step b) can result from a sliding movement of these invasive electrodes relative to the support, the support having been immobilized by being pressed on the surface of the eye. In particular, this immobilization can result from the complementary shapes of the locating mark and the limbus of the eye.

In a preferred embodiment, the invasive electrode or electrodes constitute injection needles, and the electroporation method comprises a step of injection of the product. This injection step can take place before, during or after step c).

BRIEF DESCRIPTION OF THE FIGURES

Other features and advantages of the invention will become clear upon reading the following detailed description and by examining the attached drawing, in which:

FIG. 1 shows, in perspective, a first embodiment of an injection device according to the invention for injection, with electroporation, of a product into a ciliary muscle of an eye;

FIG. 2 shows a plan view of this device;

FIGS. 3 and 4 show, along the transverse median plane A-A and the transverse plane B-B shown in FIG. 2, cross sections of the device shown in FIG. 1;

In FIG. 7, it is possible to visualize the angle β between the direction of penetration of an injection needle at the point of penetration into the eye and the direction of this injection needle;

In FIGS. 10 and 11, the device has been shown in a position of use, that is to say at the end of the stage of penetration, the spherical envelope S schematically representing the sclera of an eye, and Co schematically representing the cornea of this eye.

In FIG. 11, only the parts of the needles situated inside the spherical envelope S are shown, in broken lines.

In the various figures, identical reference signs are used to designate identical or similar elements. In FIG. 5, the reference signs are complemented by a ' sign. In FIG. 8, they are complemented by a " sign.

Definitions

Figure 5:
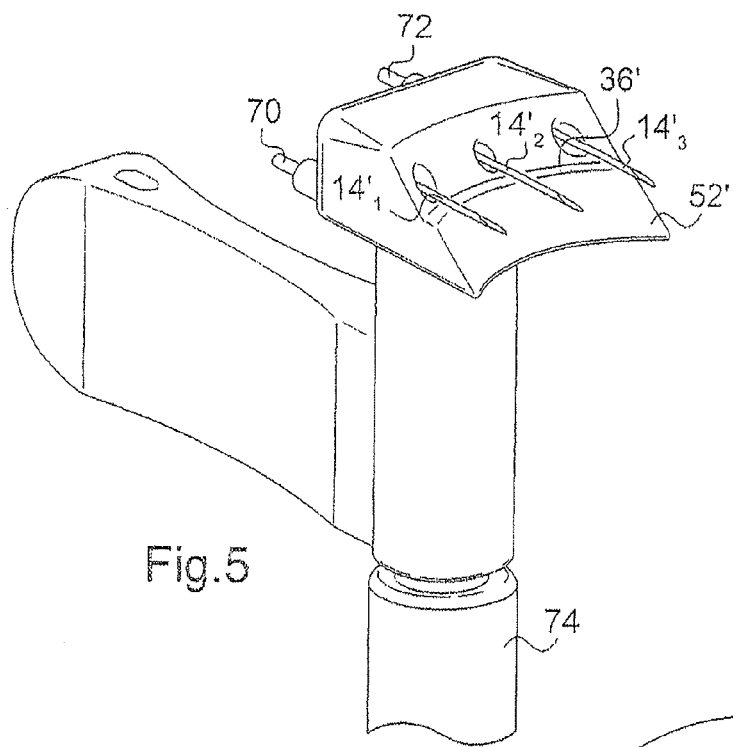
FIG. 5 shows, in perspective, a second embodiment of a device according to the invention.

The "stage of penetration" of an injection needle corresponds to the entire stage during which the injection needle penetrates "normally" into the eye.

"Normal penetration" of the injection needle is understood as a penetration substantially in the local direction of the injection needle at the point of penetration of this injection needle into the eye, that is to say at the point on the surface of the eye through which the injection needle passes this surface. Such a penetration corresponds to the movement for which an injection needle is designed, so as to avoid the insertion of the needle needlessly damaging the surface of the eye.

The locating mark and the injection needle can be designed such that, throughout the stage of penetration of said injection needle into the eye, the local direction of the injection needle at the point of penetration into the eye forms, with the direction of its forward movement at said point of penetration, or "direction of penetration", an angle β that is always less than an angle of maximum spacing $β_{max}$ of 15°, preferably 10°, or 5°.

The "local direction of the injection needle at the point of penetration into the eye" is defined by the tangent to the injection needle at the point of the eye through which the needle penetrates into the latter. In the case of a rectilinear needle, this direction is defined by the axis of the needle.

The "direction of the forward movement at the point of penetration" is the direction of the speed vector of the region of the needle situated at said point of penetration. When the needle penetrates by means of a rotation of the support about a bearing point, this direction is thus defined by the tangent, at the point of penetration, to the circle centered on this bearing point and passing through said point of penetration.

For example, with a rectilinear needle, "normal" penetration corresponds to a movement of the needle along the axis of the needle. The direction of penetration then forms a constant angle, throughout the stage of penetration, with the surface of the eye at the point of penetration of said injection needle. This angle can be 90°, although "normal" penetration is not limited to this angle.

The stage of penetration preferably lasts from the first contact of the injection needle with the surface of the eye until a position of use.

The "main axis" of a surface is the direction perpendicular to a surface passing through its center.

In the present description, the adjectives "upper" and "lower" are defined with respect to a vertical direction V as shown in FIGS. 1, 3 and 4.

The adjectives "right-hand" and "left-hand" are defined with respect to the view in FIG. 2.

A "quadrant of a hemisphere" designates a quarter of the surface of this hemisphere obtained by cuts in two perpendicular planes that intersect along the main axis of the hemisphere.

In the present description, unless otherwise stated, "comprising a" should be understood as "comprising at least one".

DETAILED DESCRIPTION OF AN EMBODIMENT

The injection device 10 shown in FIGS. 1 to 4 comprises a support 12 on which are fixed three identical and rectilinear injection needles $14_1$, $14_2$ and $14_3$ oriented parallel to one another in a needle direction $D_{needle}$.

The three injection needles belong to one and the same plane, called the "plane of the needles" and designated $P_{needles}$.

In order to be secured on the support 12, the injection needles are sandwiched between a main part 12a of the support 12 and a blocking piece 12b, which is fixed on the main part 12a, for example by clipping, by adhesive bonding or by fusion of material.

The needle $14_2$ extends at an equal distance between the needles $14_1$ and $14_3$. The distance $d_1$ between the needle $14_2$ and the needles $14_1$ and $14_3$ can be greater than 3 mm or 3.5 mm or 4 mm and less than 6 mm or 5.5 mm. In particular, it can be about 4.5 mm (FIG. 2).

Since the three needles are identical and are fixed in a described in detail, with reference to FIG. 4. For a given reference sign, the indices "1", "2" and "3" relate to the injection needles $14_1$, $14_2$ and $14_3$, respectively.

Figure 11:
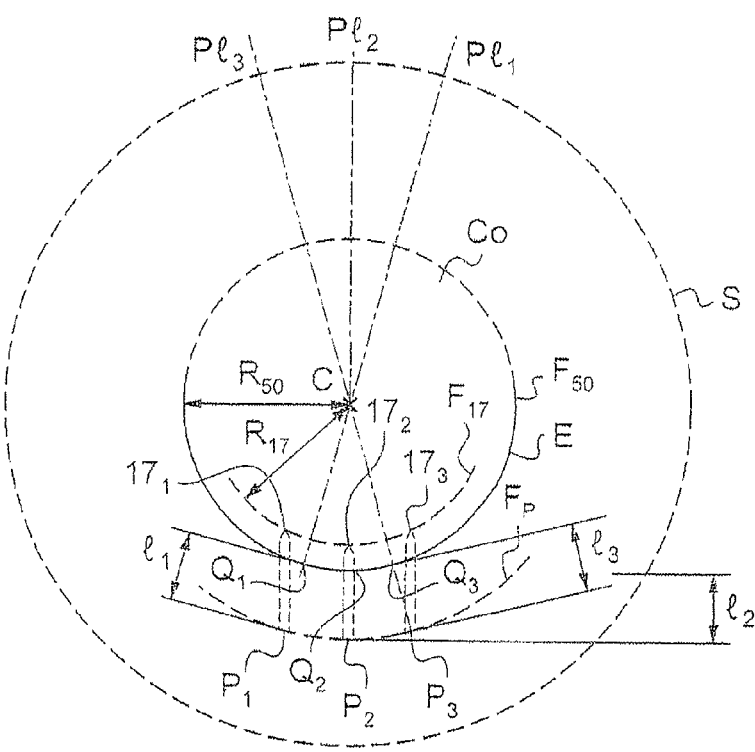
FIG. 11 shows a partial view of the device depicted in FIG. 10, as observed along the axis $Dc_0$ by the observer Obs in FIG. 10.

The needle $14_1$ extends from a proximal end $16_1$, embedded in the support, to a distal end $17_1$ with a beveled tip, for facilitating the penetration of the needle into the eye, and opening out via an axial ejection orifice. The distal ends $17_1$, $17_2$ and $17_3$ of the three needles $14_1$, $14_2$ and $14_3$ extend substantially in an arc of a circle $F_{17}$, as is shown in FIGS. 2 and 11. The needle $14_1$ is traversed in the normal way by a lumen $18_1$, which is designed for the transfer of product from the proximal end to the distal end. The external diameter of the needle $14_1$ is, for example, about 0.3 mm.

The injection needle $14_1$ comprises a protruding part $22_1$, that is to say protruding from the support, and an engaged part $24_1$, embedded in the support. The length $l_{22}$ of the protruding part $22_1$ can be, for example, between 3.3 and 3.7 mm, an ideal length being 3.5 mm. The protruding parts of the three injection needles can have a substantially identical length.

The protruding part $22_1$ of the needle $14_1$ is covered along part of its length by an insulating cover $34_1$. The insulating cover $34_1$ can continue along the engaged part of the injection needle $14_1$ and can even completely cover this engaged part.

The proximal ends of the needles open into a common distribution channel 20 in fluid communication with the outside of the support. The distribution channel 20 thus allows product to be delivered from outside the support to the proximal ends of the injection needles, and then, by way of the lumens of these injection needles, to the distal ends of the injection needles. The diameter $d_{20}$ of the distribution channel 20 can be greater than 0.5 mm or 0.6 mm and/or less than 0.9 mm or less than 0.8 mm, an ideal diameter being 0.7 mm.

The device also comprises means (not shown) for plugging one or more of the needles or for plugging the inlet of the distribution channel 20.

The injection needles protrude from the support 12 through an insertion face 26 of substantially spherical shape, that is to say carried by a spherical envelope, so as to remain spaced apart from the surface of the eye in the position of abutment of the support, such that the user can observe the point of penetration of the needle.

The insertion face 26 is inclined with respect to the direction $D_{needle}$, and it then joins an intermediate face 36 which is substantially flat, substantially parallel to the plane of the needles $P_{needles}$ and spaced apart by a defined distance $d_{36}$ from this plane, in such a way that the distance between the locating mark, in the form of a band 50 which will be described later, and the points of penetration of the different needles into the spherical envelope S, corresponding substantially to the surface of the eye in the position of abutment of the support, is about 4 mm.

Figure 6:
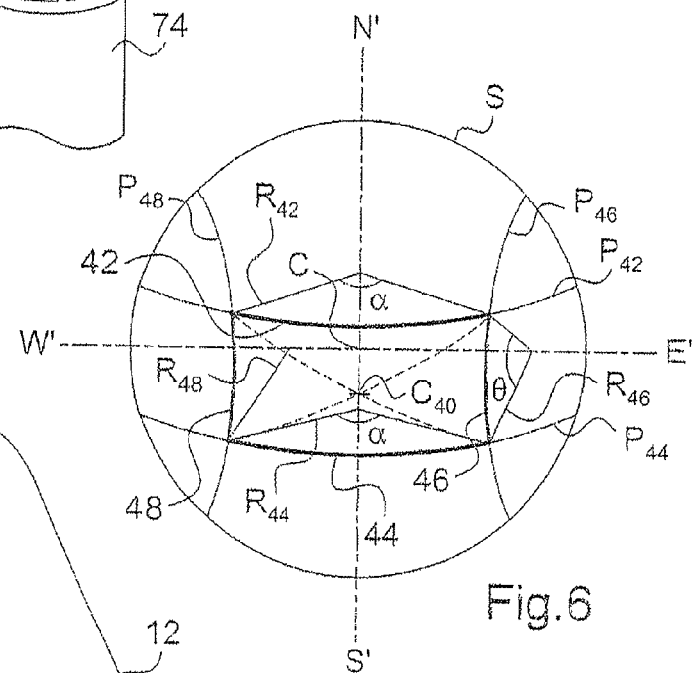
FIG. 6 shows the shape of an abutment face of a device according to the invention, in a preferred embodiment.
Figure 10:
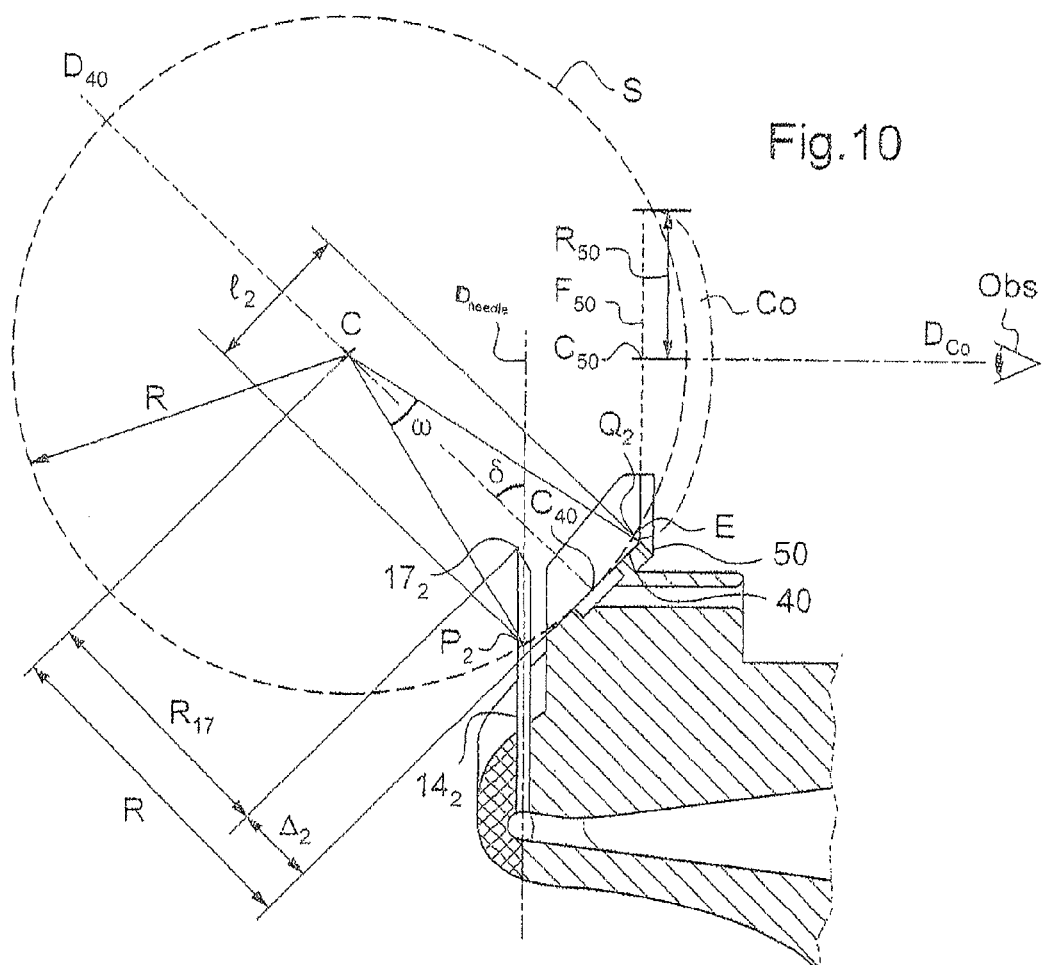
FIG. 10 shows a detail of FIG. 3.

At the opposite end from the insertion face 26, the intermediate face 36 is continued by an abutment face 40. The abutment face 40 extends along a spherical envelope S with center C and radius R, as is shown in FIGS. 4, 6 and 10. The radius R is about 14.75 mm and corresponds to the radius of the outer surface of the eye, in the region of the sclera, near the cornea.

The main axis $D_{40}$ of the abutment face 40 is the straight line intersecting the abutment face 40 perpendicularly at its center $C_{40}$. The main axis thus passes through the center C of the spherical envelope S. It is included in the median plane A-A shown in FIG. 2 (see also FIG. 10).

In the plane perpendicular to the plane of the needles $P_{needles}$ and including the needle $14_1$, the abutment face 40 extends over an angle sector $\beta$ of, for example, greater than 30° and less than 40°, for example about 36 degrees.

In the plane of the needles $P_{needles}$, the abutment face 40 extends over an angle sector $\alpha$ of, for example, greater than 80° and less than 90°.

The abutment face 40 is delimited by two large sides, namely an upper edge 42 and a lower edge 44, which are substantially parallel and circular and which extend in planes substantially parallel to the plane of the needles $P_{needles}$, and by two small sides, namely a right-hand lateral edge 46 and a left-hand lateral edge 48, which are also substantially parallel and circular and which extend in planes substantially parallel to the median plane A-A.

As is shown in FIG. 6, in which the spherical envelope S is shown, the upper edge 42 and lower edge 44 thus extend along "parallels" $P_{44}$ and $P_{42}$ with radii $R_{44}$ and $R_{42}$, respectively, the "parallels" being defined with respect to an axis N'S', while the right-hand and left-hand lateral edges 46 and 48 extend along parallels $P_{46}$ and $P_{48}$, with radii $R_{46}$ and $R_{48}$ respectively, defined with respect to an axis W'E' perpendicular to the axis N'S' and intersecting the latter at the center C.

The radius $R_{42}$ can be greater than 8 mm, or greater than 8.5 mm, or 8.8 mm, or 8.9 mm and/or less than 10 mm or less than 9.5 mm, or 9.2 mm, or 9.1 mm or even 9 mm. The radius $R_{42}$ can in particular be 8.94 mm. The radius $R_{44}$ is defined in such a way that the lower edge 44 can match the edge of the cornea.

The radius $R_{44}$ can be greater than 6 mm or 6.4 mm or even 6.5 mm and/or less than 7 mm, or 6.8 mm, or even 6.7 mm. A radius $R_{44}$ of 6.58 mm is ideal.

Seen from the front, the abutment face 40 thus has a substantially rectangular shape, of which the center $C_{40}$ is half way between the lower edge 44 and the upper edge 42 and between the right-hand lateral edge 46 and the left-hand lateral edge 48.

The corners $49_d$ and $49_g$ between the lower edge 44 and the right-hand and left-hand lateral edges 46 and 48, respectively, are preferably rounded in order to limit the risks of injury. The radius of curvature of the rounded corners can be 1 mm, for example.

The distance between the right-hand and left-hand lateral edges 46 and 48, as measured in the direction W'E', can be greater than 17 mm, 19 mm or 20 mm and/or less than 25 mm, 23 mm or 22 mm. It can be 21.11 mm, for example.

The distance between the upper edge 42 and lower edge 44, as measured in the direction N'S', can be greater than 1.9 mm, 2.2 mm, or 2.3 mm and/or less than 3 mm, 2.6 mm, or 2.5 mm. A height of 2.4 mm is ideal.

In the embodiment shown, the lower edge 44 is delimited by a band 50 of flexible material, for example of silicone. The rest of the abutment face 40 is covered by an electrically conductive cover 52.

As will be seen later in the description, the band 50 is a locating mark, and the cover 52 can serve as a non-invasive electrode.

In the sectional plane of FIG. 4, the distance $D_{50}$ between the band 50 and the point of penetration $P_1$ of the injection needle $14_1$ into the spherical envelope S is preferably greater than 1 mm, greater than 2 mm, greater than 3 mm, greater than 3.5 mm and/or less than 6 mm, less than 5 mm, or less than 4.5 mm. This feature preferably applies to each of the needles, in each case considering a sectional plane containing the needle in question and extending parallel to the plane B-B. A distance of 4 mm is ideal.

As is shown in FIG. 11, the band 50 constitutes a locating line that extends in an arc of a circle $F_{50}$ whose radius $R_{50}$ is substantially equal to the radius of the edge E of the cornea Co, that is to say preferably between 5 and 8 mm, preferably between 6 and 7 mm. The center of the arc of a circle $F_{50}$ is designated $C_{50}$. Its axis is designated "$D_{Co}$" and passes substantially through the center C of the spherical envelope on which the abutment face 40 extends.

In the position of use, the abutment face thus bears completely on the sclera of the eye, and the locating mark bears completely on the edge of the cornea.

With "i" designating the index sign of the needle $14_i$, the following designations apply:

- $P_i$ is the point of penetration of the needle $14_i$ into the spherical envelope S, corresponding virtually to the sclera of the eye;
- $Pl_i$ is the plane passing through the center C of the spherical envelope S, through the point of penetration $P_i$ and intersecting perpendicularly the arc of a circle $F_{50}$ (the median sectional plane A-A thus corresponding to the plane $Pl_2$);
- $Q_i$ is the point of the arc of a circle $F_{50}$ through which the plane $Pl_1$ intersects the arc of a circle $F_{50}$;
- $l_1$ is the distance between the points $Q_i$ and $P_i$;
- $\Delta_i$ is the minimum distance between the surface of the spherical envelope S and the distal end $17_i$ of the needle $14_i$, or "depth $\Delta_i$";
- $\omega_i$ is the angle, with the center C as its apex, between the point $Q_i$ and the point of penetration $P_i$.

In the planes $Pl_1$, $Pl_2$ and $Pl_3$, the spherical envelope S is thus intersected along a great circle, and the cornea Co, intersected through its center, has a cross section of substantially maximum area.

All the points of penetration $P_i$ of the needles $14_i$ belong to one and the same circle $F_p$. The distal ends $17_1$, $17_2$ and $17_3$ of said needles belong to one and the same circle $F_{17}$. The circles $F_{50}$, $F_p$ and $F_{17}$ are coaxial with axis $DC_0$. Whichever needle is considered, the distance between the center C and the distal end of said needle, $R_{17}$, is substantially constant. The same applies to the depth $\Delta_i$ of said distal ends with respect to the surface of the spherical envelope S. Finally, whichever needle is considered, the angle ω is substantially the same.

Whichever needle $14_i$ is considered, the distance $l_i$ is greater than 1 mm, preferably greater than 1.5 mm, more preferably greater than 1.8 mm and less than 3 mm, preferably less than 1.5 mm, more preferably less than 1.2 mm, and the depth $\Delta_i$ is greater than 0.5 mm, preferably greater than 0.6 mm, more preferably greater than 0.8 mm, and less than 1.5 mm, preferably less than 1.3 mm, more preferably less than 1.2 mm. This embodiment is particularly ideal for an injection into the ciliary muscle of the eye.

In another embodiment (not shown), whichever needle $14_i$ is considered, the distance $l_i$ is greater than 2 mm, preferably greater than 3 mm, and less than 4.5 mm, preferably less than 4 mm, or less than 3.5 mm, and the distance $\Delta_i$ is greater than 6 mm, preferably greater than 8 mm, and less than 15 mm, preferably less than 13 mm. This embodiment is particularly ideal for an injection into the vitreous body.

The angle δ, between the main axis $D_{40}$ of the abutment face and the needle direction $D_{needle}$ of the needle $14_2$ is between 50 and 60 degrees, for example about 55 degrees (FIG. 10). Advantageously, such angles δ allow the locating mark 50 bearing on the edge of the cornea to be positioned ideally for an injection into the ciliary muscle.

The angle δ, the distance $d_{36}$ and the length of the needles are determined in such a way that the needles can penetrate into the eye to a depth of greater than 700 μm and less than 3 mm in the position of abutment of the support. Advantageously, this depth permits particularly effective injection into the ciliary muscle.

The device shown also comprises a handle 60 to facilitate its manipulation. The overall length "L" of the device is, for example, about 35 mm, and its overall width "l" is, for example, about 21 mm (FIG. 3).

In the embodiment shown, the device also comprises means for electrically connecting one or more of the injection needles to the terminals of a generator of an electrical signal. For example, the two injection needles $14_1$ and $14_3$ can be electrically connected to a first of the terminals of this generator, while the central injection needle $14_2$ can be connected to the other terminal of this generator.

The device can also comprise means for electrically connecting the cover 52 to one of the terminals of the generator.

As is shown in FIG. 4, the support can in particular comprise conduits 62 permitting the introduction of pins for electrical connection to one or more of the injection needles, or to all the injection needles. The electrical current can preferably be transmitted by way of the distribution channel 20, for example if this channel comprises a wall 64 made of an electrically conductive material.

In the preferred embodiment of the invention, the three needles $14_1$, $14_2$ and $14_3$ are electrically connected to a first terminal of the generator, while the cover 52 is connected to the second terminal of this generator.

FIG. 5 shows a variant of the device described with reference to FIGS. 1 to 4. In this variant, the width of the intermediate face 36 is reduced in order to minimize the overall size and in order thereby to facilitate the positioning of the device between the two eyelids of a subject who is conscious. FIG. 5 also shows the pins 70 and 72 permitting the electrical connection, to the terminals of a generator, of a first set of electrodes formed by a cover 52' and a second set of electrodes formed by injection needles $14_1'$, $14_2'$ and $14_3'$.

The device shown in FIG. 5 also has a product reservoir 74 in fluid communication with a distribution channel (not shown) common to the three injection needles. Means (not shown) are also provided for transferring the product, for example a piston that can discharge the product out of the reservoir into the distribution channel.

Figure 8:
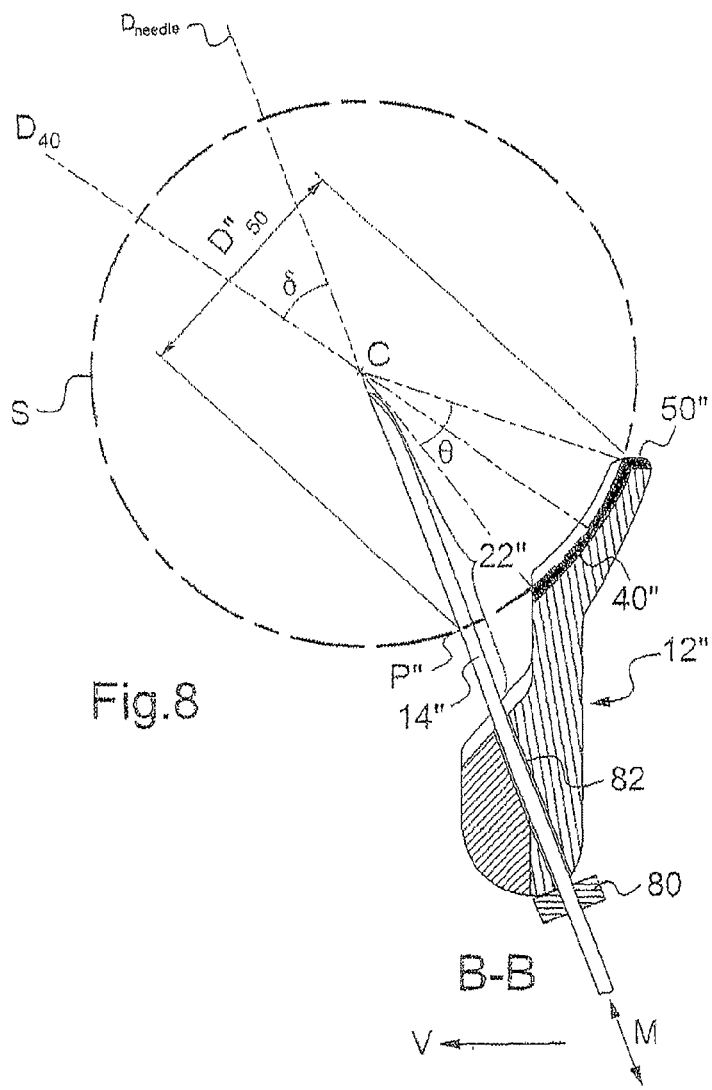
FIG. 8 shows, along a median transverse plane, a cross section of a device according to the invention in a third embodiment.

FIG. 8 shows a variant of a device according to the invention designed in particular for injection into the vitreous cavity of an eye.

The device shown in a median cross section in FIG. 8 comprises a support 12" and a single injection needle 14".

The support 12" comprises abutment means, in this case an abutment face 40" that extends along a spherical envelope S. The spherical envelope S corresponds substantially to the surface of the eye in the position of abutment of the support, in which the abutment face 40" is in contact with the surface of the eye. The center C of this spherical envelope thus corresponds substantially to the center of the eye ball.

The length of the injection needle introduced into the eye is much greater than that of the device described above, designed for an injection into the ciliary muscle. This length is preferably between 10 and 13 mm, for example about 12 mm. Such a length of the injection needle would not be able to penetrate, unless the injection needle is curved, by rotation about the band 50, without damaging the surface of the eye if the injection needle 14" were fixed on the support.

It is for this reason that the injection needle 14" is not fixed on the support but instead can slide in a through-orifice 82 of the support between a retracted position (not shown) and a needle abutment position, or "deployed position", as shown in FIG. 8.

In order to determine the needle abutment position, the injection needle 14" comprises needle abutment means 80 which can limit the length by which the protruding part 22" of the injection needle 14" projects from the support 12".

The distance $D_{50}$" between the locating mark 50" and the point of penetration P" of the injection needle 14" into the spherical envelope S is, for example, about 4 mm.

In the embodiment shown, the injection needle 14" has a length such that, in the needle abutment position, its distal end is near the center C.

In one embodiment, the device also comprises means for driving the needle from its retracted position to its deployed position. Advantageously, the deployed position can thus be achieved quickly and effectively, for example by simple manipulation of an actuating button.

The embodiment in FIG. 8 is particularly advantageous for needles that have to penetrate into the eye by a length of greater than 5 mm, greater than 7 mm, or greater than 10 mm and/or less than 15 mm.

To use a device of the kind described in FIGS. 1 to 6, the operator can proceed by the following steps:

First, the operator couples the device to a source of product, for example a syringe filled with product. He then electrically connects the first and second sets of electrodes to the two terminals of an electrical generator. The device is then ready to be applied to the eye into which an injection of product is desired.

Figure 7:
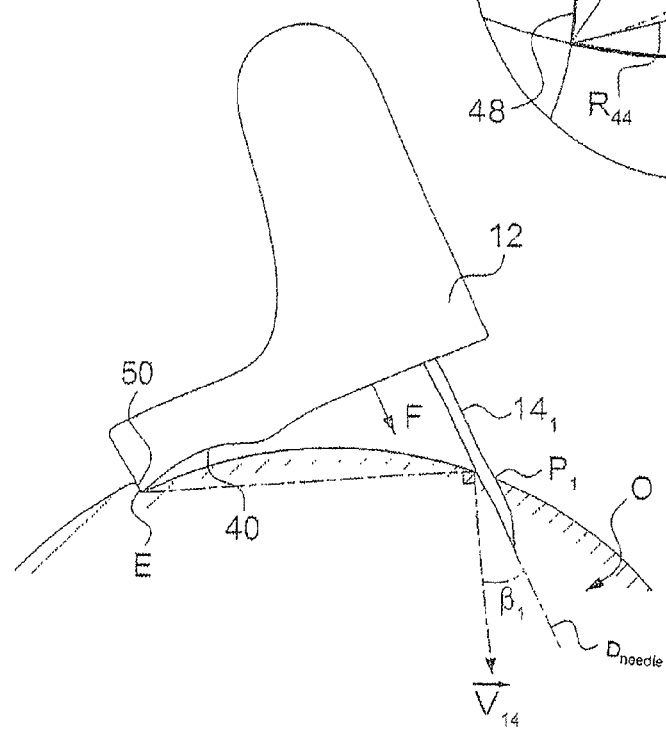
FIG. 7 is a highly schematic depiction of a device according to the invention during a stage of penetration.

To position the device, as shown in FIG. 7, the operator places the locating mark 50 on the edge E of the cornea of the eye O, taking care to ensure that the tips of the injection needles do not come into contact with the eye. The placement on the edge of the cornea advantageously permits a stable but also very precise positioning.

While keeping the locating mark 50 in contact with the edge of the cornea, the operator then causes the injection needles to penetrate through the surface of the eye by rotating the support 12 about the locating mark 50 (arrow F). The three needles penetrate substantially simultaneously through this surface.

As is shown in FIG. 7, at the point of penetration $P_1$ of the needle $14_1$ into the eye O, the direction of penetration $V_{14}$ of the needle $14_1$ forms an angle $\beta_1$ with the needle direction $D_{needle}$. The arrangement and shape of the needles $14_1$, $14_2$ and $14_3$ allow their respective directions of penetration to form, at their respective points of penetration, angles $\beta_1$, $\beta_2$ and $\beta_3$ with the needle direction $D_{needle}$ that are substantially equal to $\beta$. The length of the injection needles and/or their shape are preferably determined in such a way that, throughout the stage of penetration, in this case until the abutment position of the support, this angle remains less than 15°, preferably 10°, or 5°, regardless of the degree of engagement reached.

The shape of the abutment face, in particular the fact that it does not extend over more than one quadrant of a hemisphere, facilitates the positioning of the device and the manipulation thereof during the stage of penetration of the injection needles.

The operator continues the movement of penetration until the abutment face 40, in an abutment position of the support, comes to fit the sclera.

The inventors have shown that human eyes all have very similar dimensions and shapes and, in particular, that the distance between the ciliary muscle and the edge of the cornea of an eye is substantially the same regardless of the individual concerned. The shape and arrangement of the injection needles, of the locating mark and of the abutment face are determined such that, in the abutment position of the support, the operator is guaranteed that the ejection orifices of the injection needles open into the ciliary muscle. In the abutment position of the support, the operator then knows that the injection needles are perfectly positioned and that the product will be properly injected into the ciliary muscle. He then immobilizes the device in this position. The bearing of the abutment face 40 on the sclera and the bearing of the locating mark 50 on the edge of the cornea guarantee a good stability of the device.

The arrangement of the invasive electrodes, in this case the injection needles $14_1$, $14_2$ and $14_3$, with respect to the non-invasive electrode, in this case the cover 52, makes it possible to create an electrical field particularly effective for electroporation.

The operator can then begin the injection of the product by acting on the piston of the syringe.

The operator then sends a suitable electrical signal, for example suitable electrical impulses, by means of the electrical generator, in such a way as to create, within the injection zone, an electrical field that promotes electroporation.

The increase in the local pressure in the area of the injection points is reputed to promote the introduction of the injected product into the cells, particularly in the case of transfection. A person skilled in the art therefore generally considers it preferable to limit the number of injection points, if possible by using only a single injection needle. Surprisingly, however, the inventors have found that multiplication of the injection points promotes the penetration of the product, as can be deduced from FIG. 9. A device with three needles proves particularly effective.

Figure 9:
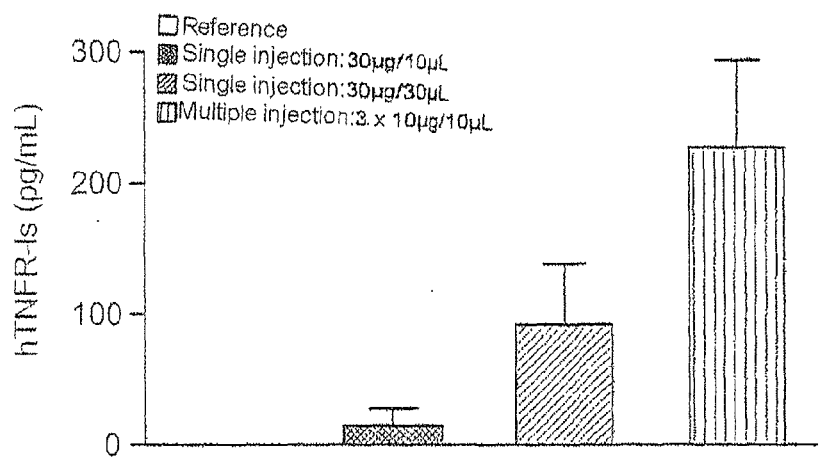
FIG. 9 shows the quantity of hTNFr-Is that has been able to penetrate into cells depending on whether the injected dose has been injected at one injection point or at several injection points.

FIG. 9 shows in fact that the result of injecting a volume of 10 μl containing 30 μg of plasmid coding for a TNF soluble receptor is inferior to that of injecting a volume of 30 μl also containing 30 μg of said plasmid (hydrodynamic effect), itself inferior to the result of injecting three volumes of 10 μl, each containing 10 μg of the plasmid, simultaneously from three injection needles.

This demonstrates that multiple injection, that is to say simultaneously through several injection points, is preferable to a single injection of an equal dose of plasmid.

When the injection of the product has been completed, the operator electrically disconnects the electrodes and the generator and then withdraws the injection needles from the eye.

The use of the device shown in FIG. 8 differs from that described for the device shown in FIGS. 1 to 6 in that the positioning of the support can be carried out independently of the penetration of the injection needle 14" into the eye.

First, as has been described above, the operator places the locating mark 50 on the edge of the cornea of the eye, then places the abutment face 40" on this surface, the injection needle 14" being in a retracted position, for example fully withdrawn from the through-orifice 82.

With the support in the abutment position of the support, the operator can then deploy the injection needle from the support and cause the distal end to penetrate into the eye, and he can then push this injection needle as far as the needle abutment position shown in FIG. 8, where the needle abutment means 80 bear on the support 12".

This embodiment of the invention has the advantage of avoiding any accidental contact of the injection needle with the surface of the eye. In addition, it permits penetration of a substantial needle length into the eye.

The other steps of injection and/or of generation of an electrical signal that promotes electroporation are identical to those described above.

The removal of the device shown in FIG. 8 is also particularly advantageous. This is because the operator, when withdrawing the injection needle 14" from the eye, can make use of the guiding action resulting from the sliding of the injection needle 14" in the through-orifice 82, acting as a slide rail for the injection needle 14". The risk of damage to the eye is then particularly low.

As will now be clear, the device according to the invention permits very precise positioning on the surface of the eye, before penetration of an injection needle and/or of an invasive electrode. It also allows said needle(s) and electrode(s) to be guided during the stage of penetration.

Of course, the invention is not limited to the embodiments described and shown, which have been provided by way of illustration.

In particular, the injection needles might not constitute invasive electrodes. The abutment face might also not carry a non-invasive electrode.

Likewise, in other embodiments, the needles might not be injection needles and might instead serve only as invasive electrodes.

In particular, the various embodiments could be combined. It would be possible in particular to use retractable needles or, more generally, needles that are able to slide on the support, with devices designed for treatment of a ciliary muscle, that is to say with relatively small needles.

Finally, the shape of the device is not limited to the one shown. The device could in particular be adapted for injection of product or electroporation in muscles other than the ciliary muscle.

The invention claimed is:

1. An electroporation device for injecting a product into a ciliary muscle of an eye having a cornea having an edge, said device comprising:
   at least one injection needle to inject said product in an injection zone;
      a support on which the at least one injection needle is fixed or which is able to guide a sliding movement of the at least one injection needle;
      a locating mark fixed on the support and disposed, along an arc of a circle with a radius of greater than 5 mm and of less than 8 mm, in such a way that said locating mark can be placed in contact with a defined bearing region of a surface of the eye, before any contact of the at least one injection needle with said surface, and can then be kept in contact with said bearing region during a stage of penetration of said at least one injection needle through said surface of the eye, the bearing region being at least a part of the edge of the cornea of the eye, said penetration resulting from a rotation of the support about the locating mark when said at least one injection needle is fixed on the support; and
      an assembly of electrodes composed of first and second sets of electrodes designed to be connected electrically to first and second terminals, respectively, of an electrical generator in such a way as to create, within the injection zone, an electrical field that promotes electroporation,
      wherein, in a position of use preventing further penetration of said at least one injection needle, said at least one injection needle penetrates into the spherical envelope via a point of penetration and extends inside said spherical envelope to a depth less than 1.5 mm.

2. The device as claimed in claim 1, wherein the length of said arc of a circle is less than 20 mm.

3. The device as claimed in claim 1, wherein, in said position of use, said at least one injection needle extends inside said spherical envelope to a depth greater than 0.5 mm.

4. The device as claimed in claim 1, wherein the support comprises an abutment face extending substantially along a spherical envelope matching the sclera of the eye.

5. The device as claimed in claim 4, wherein the at least one injection needle and a straight line intersecting the abutment face perpendicularly at its center, or "main axis of the abutment face" extend in parallel planes, and in which, in a projection in one of these planes, the direction of the at least one injection needle forms an angle of greater than 50° with the main axis of the abutment face.

6. The device as claimed in claim 4, wherein the abutment face extends laterally over an angle sector of greater than 45° and less than 135°.

7. The device as claimed in claim 4, wherein the abutment face does not extend over more than a quadrant of a hemisphere.

8. The device as claimed in claim 4, wherein the radius of curvature of said spherical envelope is greater than 9 mm, and less than 14 mm.

9. The device as claimed in claim 4, wherein the locating mark is a locating line in the shape of an arc of a circle having an axis, said axis passing through the center of said spherical envelope.

10. The device as claimed in claim 4, wherein the locating mark extends along a locating line in the shape of an arc of a circle, said at least one injection needle penetrates into the spherical envelope via a point of penetration and, in a plane passing through the center of said spherical envelope, via said point of penetration, and perpendicularly intersecting said arc of a circle, the distance between said point of penetration and the point of said arc of a circle through which said plane intersects said arc of a circle is greater than 1 mm and less than 3 mm.

11. The device as claimed in claim 4, in which said at least one injection needle penetrates into the spherical envelope via a point of penetration and, in a plane passing through the center of said spherical envelope, via said point of penetration, and perpendicularly intersecting said arc of a circle, the distance between said point of penetration and the point of said arc of a circle through which said plane intersects said arc of a circle is greater than 1 mm and less than 3 mm, said needle extending inside said spherical envelope to a depth ($\Delta_1$) greater than 0.5 mm and less than 1.5 mm.

12. The device as claimed in claim 1, wherein the locating mark is formed by a locating line that can match the edge of the cornea of the eye.

13. The device as claimed in claim 1, wherein the locating mark is designed to bear on more than 5 mm of the edge of the cornea.

14. The device as claimed in claim 1, comprising one or more non-invasive electrodes designed to come into contact with the surface of the eye, and configured so as to match the shape of the surface of the eye.

15. The device as claimed in claim 1, in which the support has a concave, substantially spherical surface being designed to serve as abutment means that are able to limit the movement of the support during the stage of penetration, and being covered, at least in part, by an electrically conductive cover that serves as an electrode.

16. The device as claimed in claim 1, wherein said first set of electrodes comprises a plurality of invasive electrodes.

17. An electroporation device according to claim 1, comprising an invasive electrode which is able to be guided in a sliding movement on the support.

18. Method for injecting a product into a ciliary muscle of an eye using the device claimed in claim 1, said method comprising:
   a) placing the locating mark in contact with a bearing region of the surface of the eye,
   b) causing the penetration of said at least one injection needle in the eye while keeping said locating mark in contact with said bearing region, said penetration being achieved by sliding the at least one injection needle relatively to the support, the support having been immobilized by being pressed on the surface of the eye,
   c) injecting the product,
   d) generating an electrical field between said first set of electrodes and said second set of electrodes, the electrical field being adapted to promote said electroporation.

19. An electroporation device for introducing a product into a ciliary muscle of an eye, said device comprising:
   at least three invasive electrode needles, which extend parallel to each other along a direction,
   a support which is able to guide a sliding movement of the at least three needles along the axis of the at least three needles until a needle abutment position, the support comprising an abutment face extending substantially along a spherical envelope matching the sclera of the eye, a non-invasive electrode extending along said spherical envelope,
   a locating mark which can be placed in contact with a defined bearing region of a surface of the eye, before any contact of the needles with said surface, and can then be kept in contact with said bearing region during a stage of penetration of the needles through said surface of the eye, the bearing region being at least a part of an edge of a cornea of the eye,
   at least one injection needle,
wherein, in a position of use preventing further penetration of said at least one injection needle, said at least one injection needle extends inside said spherical envelope to a depth of less than 1.5 mm.

* * * * *